United States Patent [19]

Hauser

[11] Patent Number: 5,458,469
[45] Date of Patent: Oct. 17, 1995

[54] FRICTION-FREE INFUSION PUMP SYSTEM

[76] Inventor: Jean-Luc Hauser, 1499 chemin S. Maymes, F- 06600 Antibes, France

[21] Appl. No.: 170,204
[22] PCT Filed: Apr. 28, 1993
[86] PCT No.: PCT/FR93/00413
§ 371 Date: Jun. 9, 1994
§ 102(e) Date: Jun. 9, 1994
[87] PCT Pub. No.: WO93/21976
PCT Pub. Date: Nov. 11, 1993

[30] Foreign Application Priority Data

Apr. 29, 1992 [FR] France ............... 92 05308

[51] Int. Cl.⁶ ............................................. F04B 43/08
[52] U.S. Cl. .......................... 417/474; 418/45; 604/153
[58] Field of Search .............................. 417/474, 476, 417/477.1, 477.3, 477.5, 412; 418/45, 153; 604/153, 131; 128/DIG. 12

[56] References Cited

U.S. PATENT DOCUMENTS

| | | | |
|---|---|---|---|
| 612,834 | 10/1898 | Dieckmann | 417/477.5 |
| 2,582,413 | 1/1952 | Clark | 418/153 |
| 2,752,852 | 7/1956 | Offutt | 417/474 |
| 2,818,815 | 1/1958 | Corneil | 418/45 |
| 2,915,983 | 12/1959 | Berrian | 418/45 |
| 2,958,294 | 11/1960 | Johnson | 417/476 |
| 3,669,578 | 6/1972 | Nameny | 418/45 |
| 3,922,119 | 11/1975 | Rosenquist | 417/474 |
| 3,963,386 | 6/1976 | Miamann | 418/45 |
| 4,483,666 | 11/1984 | Shubert et al. | 418/45 |
| 4,486,151 | 12/1984 | Korhonen-Wesala | 417/222.1 |
| 4,671,792 | 6/1987 | Borsanyi | 604/153 |

FOREIGN PATENT DOCUMENTS

| | | |
|---|---|---|
| 65191 | 8/1975 | Australia ............... 418/153 |
| 0019817 | 12/1980 | European Pat. Off. . |
| 0065938 | 12/1982 | European Pat. Off. . |
| 0103073 | 3/1984 | European Pat. Off. . |
| 0197179 | 10/1986 | European Pat. Off. . |
| 39532 | 11/1955 | Poland ............... 417/474 |
| 547550 | 5/1977 | U.S.S.R. ............... 417/476 |

Primary Examiner—Richard A. Bertsch
Assistant Examiner—Peter Korytnyk
Attorney, Agent, or Firm—Francis A. Sirr; Earl C. Hancock

[57] ABSTRACT

An infusion pump system for continuously injecting a medical substance contained in a supply chamber into a catheter connected to the body of the patient. The system includes a flattening means driven by a motor (10) and designed to flatten a portion (42) of the infusion tube and exert pressure in order to inject the medicinal substance into the catheter. The flattening means includes a rigid member such as a circular plate (32) of which the axis (34) has a geometrical position determined according to a hub (12) driven by the motor (10) in such a way that said axis (34) of the plate intersects the axis (14) of the hub at a fixed point (X). The plate (32) has projections (38, 40) which flatten the catheter (42) as the motor (10) rotates. A fork (43) held by a ball (44) prevents the plate (32) from rotating relative to the catheter. Friction on the walls of the catheter (42) is thus avoided and high infusion accuracy may be achieved.

6 Claims, 4 Drawing Sheets

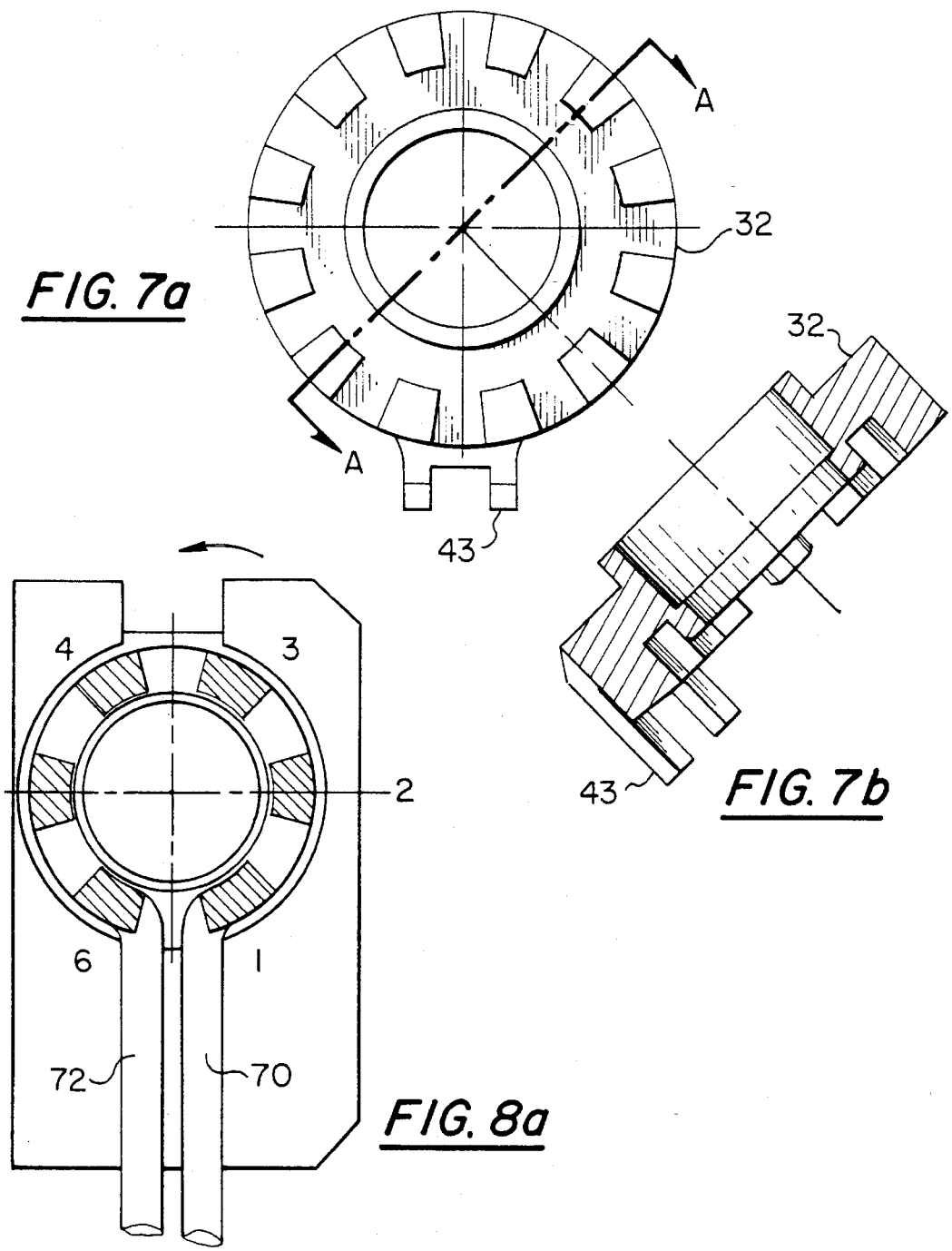
FIG. 7a
FIG. 7b
FIG. 8a
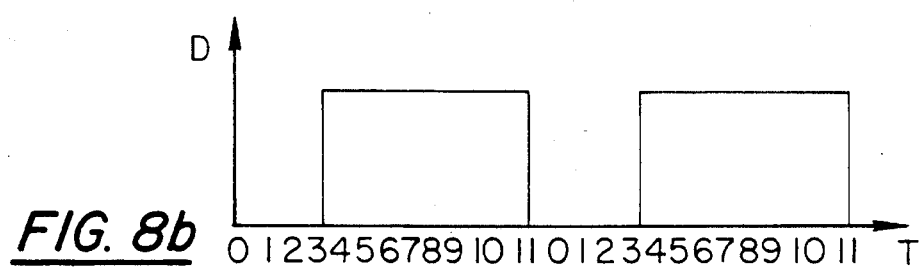
FIG. 8b

FRICTION-FREE INFUSION PUMP SYSTEM

BACKGROUND OF THE INVENTION

1. Field of the Invention

The present invention relates to an infusion pump system of the type comprising an electrical motor and a pump, for continuously injecting a medicinal substance contained in a supply chamber into a catheter connected to a patient's body, thanks to an infusion tube connected to the pump, said pump comprising flattening means driven by the motor for flattening a portion of the infusion tube so as to exert a pressure and inject the medicinal substance into the catheter.

2. Description of Prior Art

More and more human diseases are treated by injecting a medicinal substance into the patient's body. As an example, in the treatment for diabetes, it is necessary to perform at regular time intervals insulin injections to the patient. Other diseases like cancer are also treated thru injecting of medicinal substances. But frequent injections using needle and syringe are a problem with respect to the regularity of the injections to be performed, and even more, the skin damages incurred after multiple performed injections.

The solution has then been for the patient to follow a continuous treatment thanks to an infusion needle fixed at the input of the catheter connected to the patient, in general with an implanted chamber, connected to a pump.

The improvement brought about by this technique has been that the patient carries the pump along, in a pocket, or hanging from a belt. The pump driven by a small electrical motor, continuously injects the medicinal substance in the catheter and thus provides the necessary chimiotherapy, without having to always perform continuous injections thru needle and syringe.

There is currently available on the market several pump types aimed at continuous infusion of medicinal substance. The first type comprises pumps having rollers. In those pumps, rollers are generally placed at the periphery of a cylinder rotated by the electrical motor. The rollers in turn flatten a portion of the infusion tube. The system is so arranged that two or more rollers are simultaneously in contact with the infusion tube. Thus a first roller flattens the infusion tube more and more and prevents any flow within, while at the same time a second roller downstream, frees the portion of the tube previously flattened and thus induces a flow in the infusion tube, due to the pressure exerted by the flattening with the first roller. One can refer to documents EP-19816, EP-19817 and EP-197179 which deal with that same type of pump.

Pumps with rollers, although very simple, have the drawback of featuring rotating elements for exerting the flattening on the infusion tube. Inevitably, frictions occur between the rollers and the infusion tube, which leads to internal constraints within the walls of the infusion tube and consequently a permanent deformation of said walls. Consequence of the walls deformation is that metering precision for the medicinal substance to inject is impacted. Thus pumps with rollers have an accuracy of about 10 to 15%. Such a low accuracy is not acceptable for substances requiring a high injection precision.

A second type of pumps is of the type with fingers. In such a pump, several fingers flatten the infusion tube in different places and intermittently. When at least one finger flattens the infusion tube in one place, thus blocking any upstream flow in the infusion tube, at least one other finger releases downstream from the pressure it exerted on the infusion tube, and therefore enables the downstream flow of the medicinal substance, started with the flattening finger.

Pumps with fingers do not have the drawback of frictions occurring with the infusion tube walls since there is no rotating element moving along the infusion tube. Those pumps are therefore more precise than the pumps with rollers. An accuracy higher than 5% can be reached with pumps with fingers. Unfortunately the latter pumps require a mechanical driving of the fingers involving a rather complex system of cams. To still increase the accuracy of this type of pump, the number of fingers has been increased, along with the complexity of the implementing mechanics. Thus the pump described in document U.S. Pat. No. 4,671,792 has seven fingers. The complexity renders it impossible to realize a miniaturized pump with fingers. Another drawback, not the least of them, is that the complexity of the fingers driving system is accompanied with a high power consumption and thus a frequent replacing of the electrical motor batteries.

A third type of pump being also used for infusions is described in patents U.S. Pat. No. 2,818,815 and EP-A-103.073. This type of pump features a rigid part under the form of a disc coupled to the driving shaft of the pump motor and having an axis at a certain angle with said shaft, also called nutation angle. When the motor rotates, it drives the disc in an oscillatory motion such that the external rim of the disc flattens the infusion tube placed as a ring in a plan perpendicular to the motor driving shaft.

Pumps of the type above partly solve the above-mentioned drawbacks in that they do not have rotating elements such as the ones in pumps with rollers, or complex elements such as the ones required in the pumps with fingers. However, although it is mentioned in the above-referenced documents that the disc moved in an oscillatory motion does not rotate, nothing in there prevents it from rotating and thus exerting a friction on the infusion tube at the same time it flattens it. Besides, pumps as described in the prior art do not allow an accurate control of the injected substance flow.

SUMMARY OF THE INVENTION

The goal of the invention is therefore to solve the above-mentioned problems and propose a pump system for performing continuous infusion, with a high accuracy, which can be easily miniaturized and low energy consuming.

Another goal of the invention is to realize an infusion pump system having no rotating element for flattening the infusion tube so as to avoid frictions with said tube, and no complex mechanical elements, so as to be easily miniaturized and limit the power consumption.

Still another goal of the invention is to propose an infusion pump system of the type with rigid oscillating element as described in document U.S. Pat. No. 2,818,815, but which oscillating element is prevented from rotating while it is oscillating.

Yet another goal of the invention is to propose an infusion pump system of the type as described above in which the oscillating element has projections allowing an accurate metering of the medicinal substance flow.

The object of the invention is therefore an infusion pump system comprising an electrical motor and a pump designed for continuously injecting a medicinal substance contained in a supply chamber into a catheter connected to the body of a patient thru an infusion tube connected to the pump, further comprising flattening means driven by the motor for flattening a portion of the infusion tube and exert pressure in order to inject the medicinal substance into the catheter, this portion of the infusion tube being arranged in a predetermined curve shape within a plan, and the flattening means comprising a rigid oscillating element, of which the external rim corresponds to said predetermined curve shape and the geometrical position relative to the motor axis is such that the axis of the rigid element intersects the motor driving axis at a predetermined angle, the rigid element being arranged relative to the perpendicular plan so that its external rim flatten a different portion of the second part of the infusion tube while the motor is rotating, which results in injecting the medicinal substance in the infusion tube.

The oscillating element comprises blocking means in the shape of a fork held by a fixed element preventing any rotating motion of the rigid element relative to the plan perpendicular to the driving axis, so as to avoid any friction of the rigid element on the portion of the infusion tube being flattened.

BRIEF DESCRIPTION

The invention will be better understood from the following detailed description read in conjunction with the following schematics:

FIG. 7a is a bottom view of the oscillating element with 12 projections of FIG. 6;

FIG. 7b is a cross sectional view of the oscillating element with 12 projections of FIG. 7a; and FIGS. 8a and 8b provide a rough sketch of an oscillating element with 6 numbered projections and the graph versus time of the flow of injected medicinal substance when using such an oscillating element.

DESCRIPTION OF THE PREFERRED EMBODIMENTS

Figure 1:
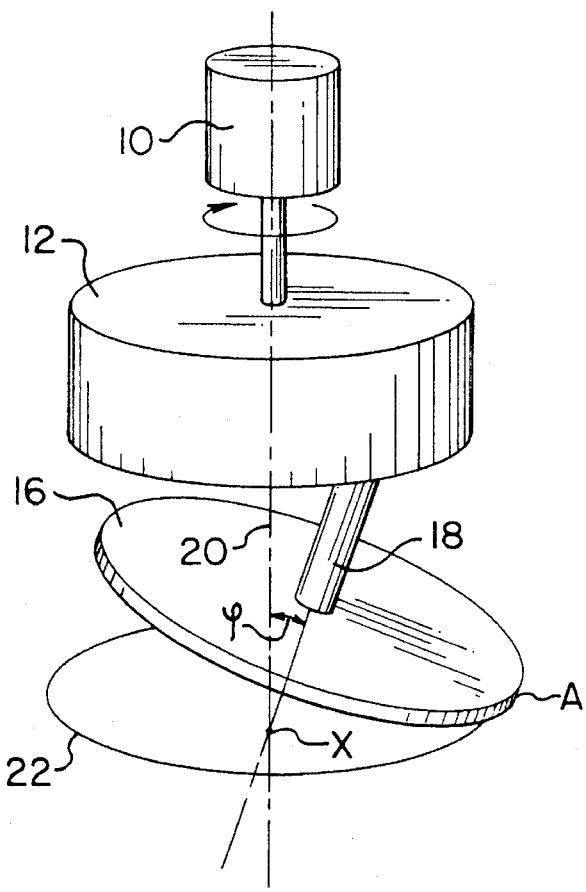
FIG. 1 is a rough sketch illustrating the principle of the pump system according to the invention.

The principle of the invention is illustrated in figure 1. An electrical motor 10 rotates a hub 12 thru a shaft 14. A rigid disc 16, preferably made of metal, is connected to the hub 12 by its axis 18 at an eccentric point on the bottom part of hub 12, said point being preferably at half the radius of the hub. The axis 18 is in a geometrical position fixed with respect to hub 12 but is free to rotate around itself. Axis 18 presents a nutation angle PHI comprised between 3 and 8 degrees with the hub axis 20 so that disc 18 present the same angle with a plan perpendicular to the hub axis. The latter plan is represented on the figure as being horizontal. Axis 18 intersects with axis 20 at a point X the position of which is precised below.

Rotated by motor 10, the hub 12 drives the disc 16 in a rotating motion around axis 20 so that its lower point describe a circle 22 in the plan perpendicular to the hub axis. This is obtained by having axis 18 of the disc 16 intersecting the axis 20 of the hub 12 (which besides results in the axis 18 describing a cone with and axis 20 and a summit X). The intersection point X is preferably in the plan of circle 22. Infact, the characteristic stated above is still true if the intersection point X is not in the plan of circle 22 but slightly above or underneath it.

The characteristic obtained thru the structure roughly sketched in FIG. 1, according to which the lower point A of disc 16 describes a circle 22 can be exploited as follows. If, in place of circle 22, a tube is placed or any other element that can be flattened, this tube or element will be flattened by disc 16 at point A. This flattening of the tube will be friction-free from the side of disc 16 under the condition that disc 16 is prevented from rotating around its axis 18 when the latter is describing a cone of summit X, while the whole system is driven by motor 10. This characteristic can be used to flatten a tube connected on one side to an infusion liquid supply chamber, and on the other side to a catheter connected to a patient, so as to continuously inject the infusion liquid within the catheter.

Figure 2:
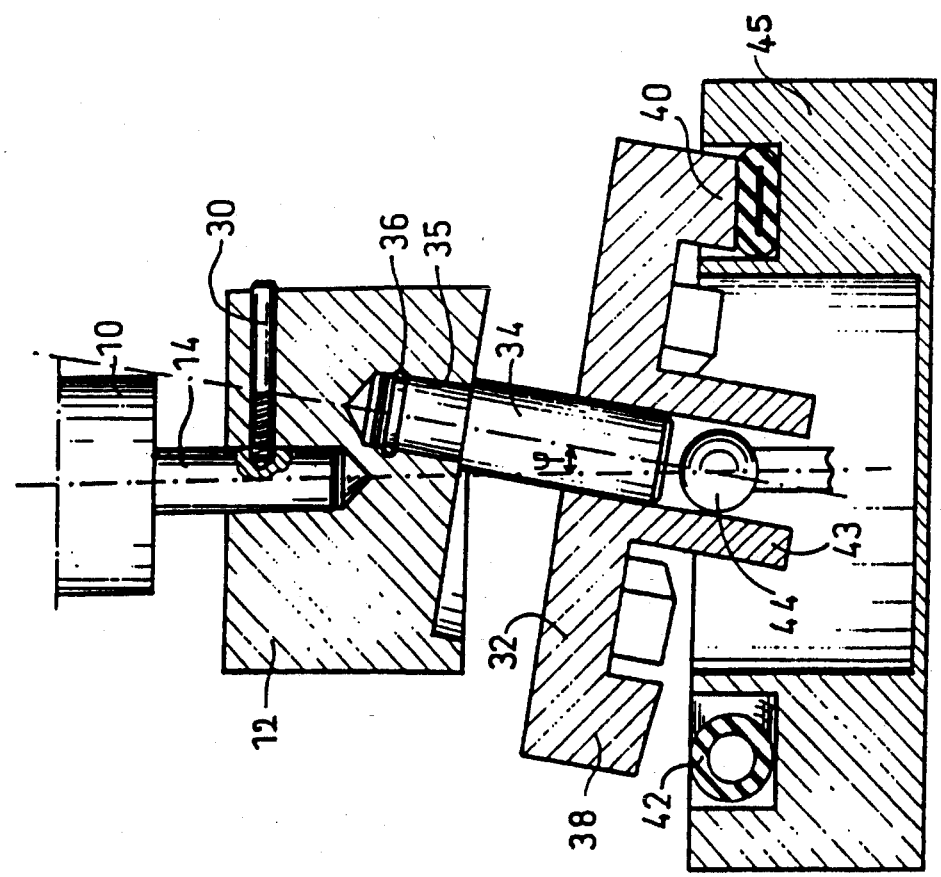
FIG. 2 represents a cross sectional view of an embodiment of the pump system according to the invention.

The practical implementation of a pump system based on the principle illustrated in FIG. 1, will now be described with respect to FIG. 2. FIG. 2 is a cross sectional view of a preferred embodiment of pump system according to the invention. As already illustrated in FIG. 1, motor 10 is connected to hub 12 thru the shaft 14. The shaft 14 is fixed in the hub 12 by a bolt or screw 30 or any other appropriate means.

A circular plate 32 (corresponding to the disc 16 in FIG. 1) is kept in a predetermined geometrical position with respect to hub 12 thanks to a shaft 34 lodged in a cavity 35 of the hub 12, but free to rotate around itself. Shaft 34 is prevented from detaching from hub 12 thanks to a joint 36 fitting in a groove placed at the bottom of cavity 35 aimed at receiving shaft 34. As will be seen further in the description, the circular plate 32 features projections 38, 40. As explained with respect to FIG. 1, the circular plate corresponding to disc 16 in FIG. 1 is in motion, when the motor rotates hub 12, in an oscillating motion such that the axis of shaft 34 which intersects the axis of shaft 14 in a fixed point X, describe a cone of summit X. During this motion, the circular plate 32 has a lower point, which describes a circle located in a plan perpendicular to the axis of shaft 14. In the preferred embodiment of FIG. 2, the lower point coincides with the external face of one projection which changes throughout the motion. The external face of the projection, when the latter is in low position, flattens then the infusion tube a portion of which is located at the circle described by the lower point of circular plate 32. Thus, as illustrated in FIG. 2, projection 40 when in low position flattens the infusion tube 42 placed in a groove of supporting stand 45. As the circular plate features a plurality of projections, other projections are in the position for flattening the infusion tube, some of them downstream with respect to projection 40 and being at the initial flattening phase while others upstream with respect to projection 40 are already in the releasing phase of infusion tube, all this resulting in the medicinal substance flowing down the infusion tube.

As has been assigned in the goals of the invention, the system as illustrated in FIG. 2 is designed to be frictionfree with respect to the infusion tube. To achieve that, it is necessary that the circular plate 32 be prevented from rotating around its axis. This preventing is obtained with a fork 43 rigidly locked with the circular plate, which is continuously engaged with a ball (44) but without being interlocked with it. When motor 10 rotates the hub 12, the shaft 34 rotating freely in cavity 35 of the hub 12 does not have a rotating motion relative to the horizontal plan in which the infusion tube is located, since the fork 43 held by the ball 44 prevents the circular plate 32 from rotating. On the contrary, shaft 34 has a rotating motion relative to the hub as a reference. A lubricating coat such as 'Teflon' needs then be deposited on the portion of shaft 34 inserted in hub 12, or on the walls of cavity 35.

Figure 3:
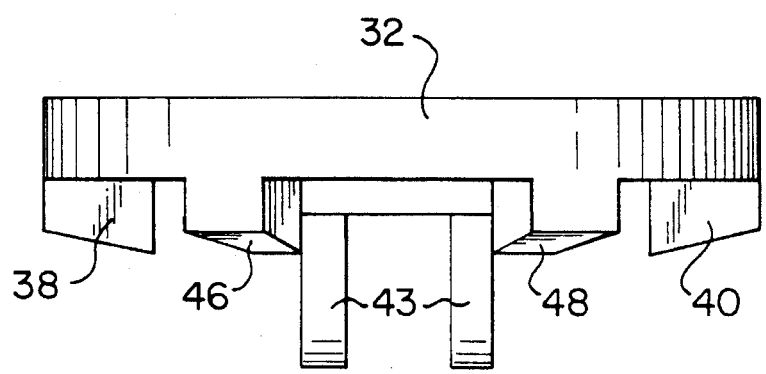
FIG. 3 is a vertical cross sectional view of the circular plate used as flattening means in the embodiment of the pump system of FIG. 2.

FIG. 3 represents the circular plate 32 in a vertical cross sectional view. This circular plate features 6 projections, of which 4 can be seen, projections 38 and 40 being illustrated on FIG. 2, the projections 46 and 48, and two other projections hidden by the projections 46 and 48. Is also illustrated on the figure, the fork 43 which prevents the circular plate 32 from rotating around itself. The end surfaces of these projections can be at an angle with respect to the middle plan of the circular plate so as to be essentially parallel to the plan of the infusion tube, when a given projection is in the lower position and flattens the infusion tube. These end surfaces can also be rounded so as to not damage the infusion tube.

Figure 4:
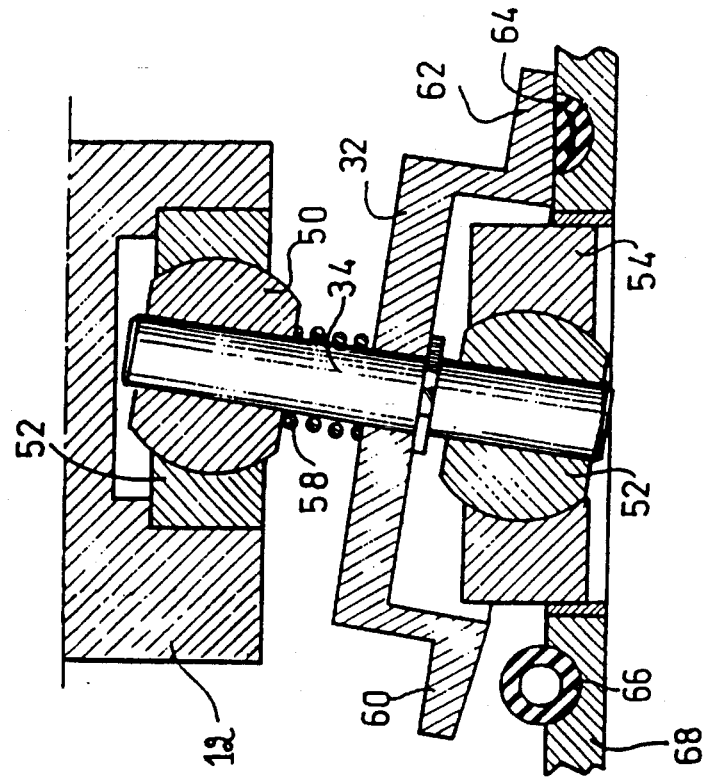
FIG. 4 is a cross sectional view of another embodiment of the pump system according to the invention.

A second embodiment is represented in cross section on FIG. 4. As illustrated, shaft 34 of the circular plate 32 is mounted within the hub 12, of which only a portion has been represented, thanks to a ball and socket joint. A ball 50 interdependent with the shaft 34 can move freely within a socket 52 of the hub 12. In the same fashion, the other end of the shaft 34 is interdependent with a ball 52 which can move freely in a cavity 53 of a fixed stand 54. The circular plate 32 is blocked by a nut 56 on one hand, and maintained adjacent said nut by a spring 58 on the other hand. In the same fashion as in the embodiment represented with FIG. 2, the circular plate 32 features projections among which the projections 60 and 62, the projection 62 being represented when in its position of flattening the infusion tube 64. The latter is received within a groove 66 of a supporting stand 68.

Figure 6:
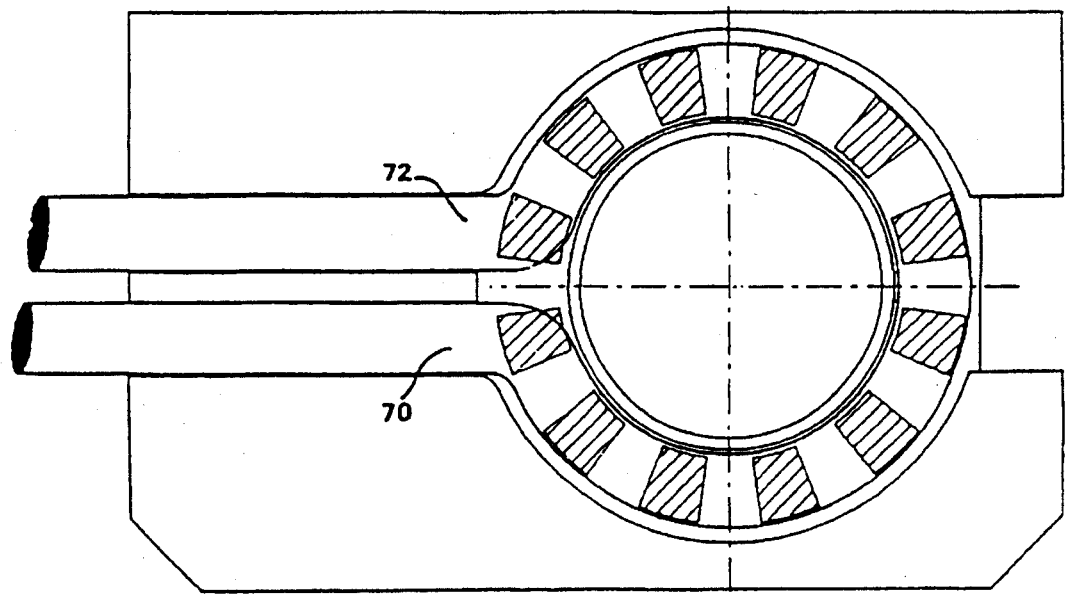
FIG. 6 is a top view providing a rough sketch of the portion of the infusion tube flattened by an oscillating element with 12 projections and the placing of the projections relative to the infusion tube.
Figure 5:
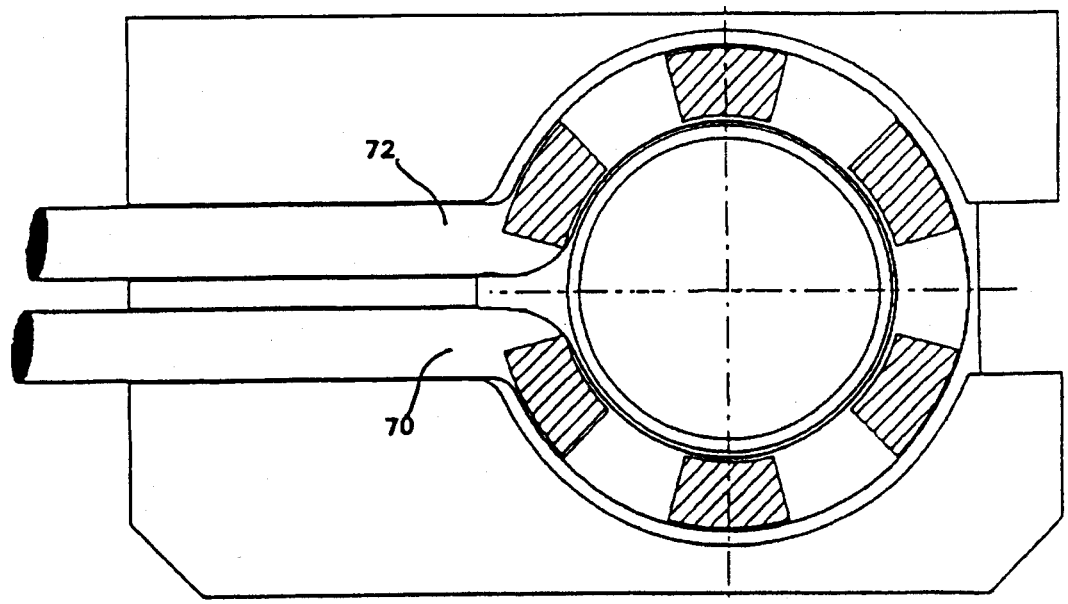
FIG. 5 is a top view providing a rough sketch of the portion of the infusion tube flattened by an oscillating element with 6 projections and the placing of the projections relative to the infusion tube.

The number of projections can vary as will be seen hereafter. But whatever this number, the projections must be distributed around the circular plate so that none of the projections reside above the location inbetween input and output of the infusion tube where obviously there is no tube potion to flatten. Thus, it can be seen either on FIG. 5 representing the ring portion of the infusion tube between its input 70 and its output 72 in the case of 6 projections, or on FIG. 6 representing the same infusion tube in the case of a circular plate with 12 projections, that none of the projections resides above the location with no infusion tube between the input 70 and the output 72.

The higher number of projections in the circular plate, the higher accuracy is obtained with regulating the flow of medicinal substance. Indeed, the projections allow injecting the liquid in the infusion tube in discrete quantities under the condition that there always be one projection flattening the infusion tube. If, at a given time, no projection is in lower position, there is a risk of upstream backing of the substance along the infusion tube. It is thus necessary that when a projection is about to release its flattening, there is another projection about to reach the lower position. Under this condition, the liquid is driven within the infusion line with a higher accuracy when there is more projections to the circular plate.

Besides, the projections induce pressure peaks within the infusion tube which allow avoiding the development of blood clots at the far-end tip of the infusion tube. As represented in FIGS. 5 and 6, the aggregate surface of the projections is approximately half the aggregate surface of the circular plate. Although this percentage of 50% is preferable, it is possible to increase or even decrease it without departing from the scope of the present invention. With a percentage of 50%, the volume of liquid moved at each revolution, is about 50% of the total volume within the infusion tube in the ring. FIG. 7a is a bottom view of the circular plate 32 in the embodiment with 12 projections as illustrated in FIG. 6. FIG. 7b is a cross sectional view of the circular plate as illustrated on FIG. 7a following plan A, showing the fork 43 preventing the circular plate from rotating around itself.

The number of projections is also related to the nutation angle. A wide nutation angle (approximately 8 degrees) obviously requires projections close to each other, and therefore a large number of projections to avoid any upstream backing problems. On the contrary, if the nutation angle is narrow (approximately 3 degrees), a large number of projections is not necessary. It is to be noted that the above reasoning is applicable whatever the circular plate dimensions; however, the optimum nutation angle for a given number of projections varies according to the circular plate diameter.

FIGS. 8a and 8b illustrate the pump with a circular plate having 6 projections as in FIG. 5. On FIG. 8a, the projections have been numbered following the rotation direction of the pump indicated with an arrow. That means that the infusion tube further to the input 70 is flattened firstly by projection 1, then projection 2, and so on, so as to move the liquid towards the output 72 of the infusion tube. The flow D of liquid injected in the infusion tube from output 72 can then be represented as pulses function of time as in FIG. 8b. This comes from the fact that the injecting of liquid in the infusion tube is maximum when projections 1 to 5 are in lower position, and minimum when projection 6 gets to the lower position as illustrated in the following correspondence table between the instants T of FIG. 8 and the numbers of projections which are in the lower position:

| T ⟶ | 0 | 1 | 2 | 3 | 4 | | 10 | 11 | 0 | 1 |
|---|---|---|---|---|---|---|---|---|---|---|
| Projections in ⟶ lower position | 5,6 | 6 | 6,1 | 1 | 1,2 | ...4,5 | 5 | 5,6 | 6 | |

Although the circular plate as illustrated in the embodiments of FIGS. 2 to 8 features projections designed for flattening the infusion tube, it will be obvious to the man skilled in the art that other shapes could also be used. Thus, it is possible to design the external face of the circular plate to have a sinusoidal profile. The external face of the circular plate can be truncated or even plan as of the disc on FIG. 1, although the latter shape does not seem to lead to the better results.

In the embodiments illustrated on the figures, the portion of the infusion tube that can be flattened is a circle or a ring. However it is possible to lay the infusion tube on a plan following a curve shape different from the circle, with a disc having an external rim corresponding to this curve shape.

I claim:

1. Infusion pump system comprising an electrical motor (10) and a pump driven by said motor, designed for continuously injecting a medicinal substance contained in a supply chamber into a catheter connected to a patient's body thru an infusion tube (42) connected to the pump, said pump comprising flattening means driven by an axis (18) having with the driving shaft (14) axis of said motor a predetermined angle, said flattening means including a rigid oscillating element (16) of which an external rim thereof faces a portion of said infusion tube arranged in a predetermined curve shape (22) in a plane perpendicular to said driving shaft (14) axis, for flattening said portion of the infusion tube so as to exert a pressure and inject the medicinal substance into the catheter while the motor is rotating;

said system being characterized in that said rigid oscillating element comprises blocking means (43) in the shape of a fork held by a fixed element (44) preventing any rotating motion of said rigid element relative to the plane perpendicular to said driving shaft axis, so as to avoid any friction of said rigid element on said portion of the infusion tube.

2. The system according to claim 1, characterized in that said rigid element (16) is of a shape essentially circular and said portion of the infusion tube is arranged following the arc of a circle (22) in said plane perpendicular to the driving shaft axis.

3. The system according to claim 2, characterized in that said external rim the shape of the circular plate (32) includes projections (38, 40) which sequentially flatten said portion of the infusion tube in the shape of an arc of a circle.

4. The system according to claim 2 or 3, characterized in that the axis (18) of said rigid element (16) intersects with the driving shaft (14) axis at a point (X) located in said plane perpendicular to said driving shaft axis.

5. The system according to any of the claims 1 characterized in that said motor (10) rotates a hub (12), and said rigid element carries a shaft (34) mounted free in a cavity of said hub so as to be able to rotate around its axis within said cavity when the hub is driven by the motor.

6. The system according to any of the characterized in that said motor (10) rotates a hub (12), and said rigid element carries a shaft (34) mounted free in said hub with a ball (50) so as to be able to rotate around its axis when said hub is driven by said motor.

* * * * *